United States Patent [19]

Ziegenhorn et al.

[11] 4,247,630

[45] Jan. 27, 1981

[54] METHOD AND REAGENT FOR THE DETERMINATION OF URIC ACID

[75] Inventors: Joachim Ziegenhorn, Unterpfaffenhofen; Eberhard Munz, Polling; Brigitte Draeger; Alexander Hagen, both of Tutzing; Wolfgang Gruber, Tutzing-Unterzeismering, all of Fed. Rep. of Germany

[73] Assignee: Boehringer Mannheim GmbH, Mannheim-Waldhof, Fed. Rep. of Germany

[21] Appl. No.: 892,360

[22] Filed: Mar. 31, 1978

[30] Foreign Application Priority Data

Apr. 26, 1977 [DE] Fed. Rep. of Germany ....... 2718588

[51] Int. Cl.$^3$ .......................... C12Q 1/30; C12Q 1/62
[52] U.S. Cl. ....................................... 435/10; 435/26; 435/27
[58] Field of Search ........... 195/99, 103.5 R, 103.5 U; 435/10, 26, 27

[56] References Cited

U.S. PATENT DOCUMENTS

| | | | |
|---|---|---|---|
| 3,335,069 | 8/1967 | Wachter | 195/103.5 UX |
| 3,956,069 | 5/1976 | Allain et al. | 195/99 X |

FOREIGN PATENT DOCUMENTS

2450726  5/1976  Fed. Rep. of Germany .

*Primary Examiner*—Esther M. Kepplinger
*Attorney, Agent, or Firm*—Sprung, Felfe, Horn, Lynch & Kramer

[57] ABSTRACT

The invention relates to an improvement in a conventional method for the determination of uric acid involving uricase/catalase/aldehyde dehydrogenase, resulting in the formation of produced NAD(P)H as a measure of the initial uric acid present, which improvement comprises adding at least one compound selected from oxalates, malonic acid mono-lower alkyl esters, trihaloethanols, pyrazole, pyridine, substituted pyrazole and pyridine wherein the substituents are selected from lower alkyl and halogen, pyridine carboxylic acids, pyridine carboxylic acids substituted with a lower radical, pyridine carboxylic acid amides and pyridine carboxylic acid lower alkyl esters, thiourea, isobutyramide and chelate-forming complexing agents, in order to suppress disturbance-causing creep reactions in said method. Reagents containing such additive compounds are also provided.

19 Claims, No Drawings

METHOD AND REAGENT FOR THE DETERMINATION OF URIC ACID

The present invention relates to a method and reagent for the determination of uric acid. More specifically, the invention relates to the disturbance-free determination of uric acid, especially in serum and plasma utilizing a uricase/catalase/aldehyde dehydrogenase system.

An elevated uric acid level in the serum (plasma) is an important indication of the existence of a gout disease. Therefore, the quantitative analysis of uric acid in the serum is one of the investigations which are frequently carried out in clinical-chemical laboratories.

For the enzymatic determination of uric acid, in practice there have hitherto essentially been used two methods which are known as the uricase method and the urica-quant method (cf. "Methoden der enzymatischen Analyse" ed. H. U. Bergmeyer, Volume 2, 1999–2005/1974, pub. Verlag Chemie). Recently, a new enzymatic process has been described for the determination of uric acid (see German Pat. No. 2,450,726) (Haeckel) which depends upon the following principle:

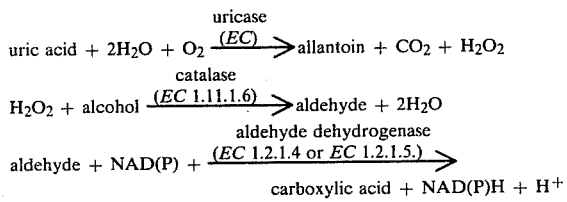

The formation of reduced nicotinamide-adenine-dinucleotide (phosphate) (NAD(P)H), measured by the extinction increase at 340 nm, Hg 334 nm or Hg 365 nm, is proportional to the amount of uric acid.

Compared with the uricase method, which is regarded as the reference method, this new process according to Haeckel is characterised by a lower susceptibility to disturbance by impurities in the analysis sample since the measurement is carried out in a longer ultra-violet wave range (334 to 365 nm instead of 293 to 297 nm). In comparison with the urica-quant process, the time required per analysis is substantially smaller so that this new method is especially suitable for the rapidly running automatic analysis devices.

However, when using the above-described Haeckel uric acid test, it has been found that, in many cases and especially in cases of kidney diseases and liver diseases, considerable disturbances of the test occurred due to creep reactions. When working according to the end value method, an NAD(P)H increase or an NADH decrease is found even before the addition of the uricase solution which serves as a starter. Furthermore, the reaction also does not stop after all of the uric acid has been consumed, further NAD(P)H being formed. The velocity of this creep reaction at 25° C. is about 0.001 to 0.004 ΔE/min. Furthermore, the velocities before the start and after the end of the uric acid reaction often differ from one another. This makes a precise evaluation of the measurement results very difficult because the extinction difference corresponding to the amount of uric acid reacted cannot be precisely ascertained. However, the analysis result is to be calculated from this extinction difference, the analysis batch and the molar extinction coefficient of NADH.

In the case of a uric acid determination by the kinetic principle, these creep reactions are even more disturbingly noticeable than in the case of a determination by the end value method. As is known, in the case of the kinetic process, a standard determination must be carried out for the calibration which is always necessary and for this purpose an aqueous standard is generally used (see J. Ziegenhorn in "Grundlagen der enzymatische Analyse", H. Bergmeyer, page 81 to 85, pub. Verlag Chemie (1977)). Since no creep reactions occur in the case of these standard analyses, in the case of the analysis of the above-mentioned sera in which creep reactions do occur, falsely positive or negative results are obtained, the uric acid reaction superimposing the creep reaction. However, kinetic tests are of great importance in automated laboratories because they enable the time needed per analysis to be drastically reduced and thus better utilize the automatic analysis devices. Furthermore, they are generally less susceptible to disturbance by turbidities or inherent colours of the sample than end value methods.

As in the case of the end value process, also in the case of the kinetic process, the disturbances caused by creep reactions can, to a certain extent, be compensated by the determination of sample blanks. However, this has disadvantages; sample blank determinations always mean a doubling of the time and reagent requirement when carrying out the analysis. Especially in modern, rapidly running automatic analysis devices, for example the Centrifugal Fast Analyzer and related apparatus, sample blank analyses very much impair the optimum utilization of the device.

Depending upon the extent of the creep reaction, errors of 5 to 20% have been ascertained in the analysis results. This means a marked limitation of the usefulness of the Haeckel method for the determination of uric acid in routine diagnosis where, as is known, uric acid tests must often be carried out on the sera of patients with kidney diseases. Especially in the case of gout, kidney diseases occur extraordinarily frequently.

Therefore, it is an object of the present invention to provide a process with which the above-described disturbances in the Haeckel uric acid determination can be avoided.

Thus, according to the present invention, there is provided a process for the determination of uric acid in biological material by means of uricase, catalase and aldehyde dehydrogenase in the presence of alcohol and nicotinamide-adenine-dinucleotide or phosphate (NAD(P)), wherein there is added at least one compound selected from oxalates, malonic acid mono(-lower) alkyl esters, trihaloethanols, pyrazole or pyridine optionally substituted with one or more lower alkyl radicals and/or halogen atoms, pyridine-carboxylic acids optionally substituted by a lower alkyl radical and the amides and lower alkyl esters thereof, thiourea, isobutyramide and chelate-forming complexing agents, such as nitrilotriacetic acid and ethylenediamine-tetraacetic acid.

The biological materials to which the process of the present invention can be applied include, in particular, serum and blood, as well as urine and liquids obtained by cell digestion or the like.

According to the present invention, lower alkyl radicals are to be understood to mean those containing up to 4 carbon atoms and halogen atoms are to be understood to mean chlorine, bromine and iodine atoms. In the case of the pyrazole derivatives, those are preferred in which the substituent is in the 4-position and in the case of the pyridine-carboxylic acids, the carboxyl group is in the 3-position. Typical examples for compounds which can be used include pyrazole, 4-bromopyrazole, 4-iodopyrazole, 4-chloropyrazole, 4-methylpyrazole, 4-ethylpyrazole, 4-propylpyrazole, 3,4-dibromopyrazole, pyridine, N-methylnicotinamide and the like.

The additives used according to the present invention can be used individually or as mixtures. Whereas in many cases, a single additive suffices in order to suppress a creep reaction completely, the addition of at least two of the additives is, nevertheless, preferred. It is especially preferred to use an oxalate or a malonic acid mono(lower) alkyl ester, together with at least one additive selected from complexing agents, trihaloethanols, isobutyramide, thiourea, substituted and unsubstituted pyrazoles, pyridines and pyridine-carboxylic acids. In the case of the oxalates, the alkali metal salts are preferred.

The process can be carried out according to the end value process in which the concentration of the uric acid is determined after termination of the reaction from the measured extinction difference. Furthermore, kinetic processes can be employed in which the velocity of the reaction serves as measurement value. The manner in which such kinetic test systems are to be built up in the case of the presence of coupled enzyme reactions is described in German Pat. No. 2,553,536. Furthermore, from German Pat. No. 2,440,011, it is already known that the Michaelis constant of uricase with regard to uric acid, which is too low for use in kinetic processes, can be apparently increased by the addition of a competitive inhibitor so that kinetic measurement principles can be utilized. Such a competitive inhibitor can be, for example, xanthine.

The additives used according to the present invention are employed in such amounts that creep reactions which would otherwise occur are completely suppressed. The amounts necessary can easily be determined by simple preliminary experiments. In general, however, it is sufficient to add from 0.005 to 0.5 mol of additive per liter of reagent. However, in individual cases, larger or smaller additions can be used.

The process conditions with regard to pH value, time, temperature and the like correspond to those disclosed in German Pat. No. 2,450,726. It is preferable to operate at a pH of from 8.0 to 9.0, using a buffer which has its maximum capacity in this pH range, especially good results having been achieved with the use of diphosphate buffer ($K_4P_2O_7$/HCl). The determination is preferably carried out at ambient temperature.

The present invention also provides a reagent for the determination of uric acid, which comprises uricase, catalase, aldehyde dehydrogenase, alcohol, NAD(P) and buffer, together with at least one compound selected from oxalates, malonic acid mono(lower) alkyl esters, trihaloethanols, pyrazole and pyridine optionally substituted with one or more lower alkyl radicals and/or halogen atoms, pyridine-carboxylic acids optionally substituted by a lower alkyl radical and the amides and lower alkyl esters thereof, thiourea, isobutyramide and chelate-forming complexing agents, such as nitrilotriacetic acid and ethylenediamine-tetraacetic acid.

A preferred reagent of the above-mentioned type comprises about $1 \times 10^2$ to $1 \times 10^3$ U/liter uricase, 500 to 1500 kU/liter catalase, 500 to 1000 U/liter aldehyde dehydrogenase, 0.3 to 2 mol/liter ethanol, 0.5 to 1.5 mMol/liter NAD+ or NADP+· 20 to 100 mMol/liter buffer (pH 8.0 to 9.0) and 0.005 to 0.5 mol/liter of additive according to the present invention.

According to the present invention, it is possible, as described above, to exclude creep reactions which impair the uric acid determination and thus to improve the exactitude of the process and to reduce the time and reagent requirements by avoiding the necessity of sample blank determinations.

The following Examples are given for the purpose of illustrating the present invention:

EXAMPLES 1 to 27

The following described Examples were carried out according to the end value process, using the following reagents:

Reagent 1

$K_4P_2O_7$/HCl buffer (30 to 50 mMol/liter; pH 8.0 to 9.0), ethanol (0.3 to 2 mol/liter), NAD+ ($\geq 0.5$ mMol/liter), catalase from bovine liver ($\geq 500$ kU/liter), aldehyde dehydrogenase from yeast ($\geq 500$ U/liter).

Reagent 2

Uricase from pig liver ($\geq 1.6 \times 10^5$ U/liter).

Determination batch

Measurement irradiation: Hg 334 nm, 340 nm, Hg 365 nm; layer thickness of the cuvette: 1 cm; incubation temperature: ambient temperature.

2.0 ml. of Reagent 1 are pipetted into a cuvette, 0.1 ml. of sample is added thereto and mixed. The extinction is registered for about 3 minutes, extrapolated to the point of time of the addition of Reagent 2 and $E_1$ is determined. 10 µl. of Reagent 2 are admixed. The extinction is registered for about 2 to 10 minutes and $E_2$ is determined by extrapolation to the point of time of the addition of Reagent 2.

Calculation of the concentration (c) of the uric acid in the serum:

| | |
|---|---|
| c = ($E_2$ − $E_1$) . 3.41 mMol/l. | (λ = Hg 334 nm) |
| c = ($E_2$ − $E_1$) . 3.35 mMol/l. | (λ = Hg 340 nm) |
| c = ($E_2$ − $E_1$) . 6.20 mMol/l. | (λ = Hg 365 nm, NAD) |
| c = ($E_2$ − $E_1$) . 6.03 mMol/l. | (λ = Hg 365 nm, NADP) |

SAMPLE MATERIALS

Serum, plasma and diluted urine.

In the case of the process carried out as described above, there were added the additives mentioned in the following Table, which states the nature of the sample material employed, the coenzyme used and the additive used, as well as the non-specific extinction change (creep reaction) in ΔE per minute. Examples 1, 4, 6, 8, 10, 13, 17, 22, 24 and 25 are comparative Examples and the other Examples illustrate the present invention:

| Example No. | sample | Coenzyme | additive (Mol/l.) | creep reaction ΔE/minute |
|---|---|---|---|---|
| 1 | uraemic serum No.1 | NAD | — | +0.004 |
| 2 | uraemic serum No.1 | NAD | pyrazole (0.05–0.3) | 0.000 |
| 3 | uraemic serum No.1 | NAD | pyridine (0.05–0.20) | 0.000 |
| 4 | uraemic serum No.2 | NAD | — | +0.002 |
| 5 | uraemic serum No.2 | NAD | 4-methylpyridine (0.1–0.3) | 0.000 |
| 6 | uraemic serum No. 3 | NAD | — | +0.003 |
| 7 | uraemic serum No.3 | NAD | (a) pyrazole (0.05–0.15) | +0.001 |
|   |   |   | (b) sodium oxalate (0.05–0.15) | 0.000 |
| 8 | uraemic serum No.4 | NAD | — | +0.002 |
| 9 | uraemic serum No.4 | NAD | trichloro-ethanol (0.01–0.07) | 0.000 |
| 10 | uraemic serum No.5 | NAD | — | −0.003 |
| 11 | uraemic serum No.5 | NAD | sodium oxalate (0.05–0.15) | 0.000 |
| 12 | uraemic serum No.5 | NAD | malonic acid monoethyl ester (K-salt) (0.05–0.15) | 0.000 |
| 13 | uraemic serum No.6 | NAD | — | +0.003 |
| 14 | uraemic serum No.6 | NAD | (a) pyrazole (0.05–0.15) | +0.001 |
|   |   |   | (b) malonic acid monoethyl ester (K-salt) (0.05–0.15) | 0.000 |
| 15 | uraemic serum No.6 | NAD | (a) pyrazole (0.05–0.15) | +0.001 |
|   |   |   | (b) pyridine (0.05–0.10) | 0.000 |
| 16 | uraemic serum No.6 | NAD | thiourea (0.1–0.2) | 0.000 |
| 17 | uraemic serum No.6 | NADP | — | +0.002 |
| 18 | uraemic serum No.6 | NADP | trichloro-ethanol (0.01–0.07) | 0.000 |
| 19 | uraemic serum No.6 | NADP | (a) pyrazole (0.05–0.15) | +0.001 |
|   |   |   | (b) malonic acid monoethyl ester (K-salt) (0.05–0.15) | 0.000 |
| 20 | uraemic serum No.6 | NADP | (a) pyrazole (0.05–0.15) | +0.001 |
|   |   |   | (b) sodium oxalate (0.05–0.15) | 0.000 |
| 21 | uraemic serum No. 6 | NADP | (a) pyrazole (0.05–0.15) | +0.001 |
|   |   |   | (b) pyridine (0.05–0.10) | 0.000 |
| 22 | uraemic serum No.7 | NADP | — | +0.003 |
| 23 | uraemic serum No.7 | NADP | (a) trichloro-ethanol (0.01–0.07) | +0.001 |
|   |   |   | (b) malonic acid monoethyl ester (K-salt) (0.05–0.10) | 0.000 |
| 24 | uraemic serum No.8 | NAD | — | +0.002 |
| 25 | uraemic serum No.8 | NAD | EDTA (0.05–0.20) | 0.000 |
| 26 | serum No.9 | NAD | — | +0.001 |
| 27 | serum No.9 | NAD | isobutyramide (0.1–0.3) | 0.000 |

From the Examples 1 to 27, it can be seen that, according to the process of the present invention, disturbing creep reactions can be completely suppressed, regardless of whether they give rise to an increase or decrease of the extinction.

EXAMPLE 28

For the determination of uric acid by a kinetic method, the following reagent can be employed:

Reagent $K_4P_2O_7$/HCl buffer (30 to 50 mMol/liter; pH 8.0 to 9.0), ethanol (0.3 to 2 Mol/liter), $NAD^+$ ($\geq 0.5$ mMol/liter), catalase from bovine liver ($\geq 500$ kU/liter), aldehyde dehydrogenase from yeast ($\geq 500$ U/liter), uricase (470 to 710 U/liter), xanthine, potassium salt (180 to 240 $\mu$mol/l.).

Determination batch

The analysis is carried out by the kinetic "fixed-time process" (cf. German Pat. No. 2,558,536), using a GEMSAEC Fast Analyzer.

Measurement irradiation: 340 nm; incubation temperature: 25° C.

Sample or standard: 50 $\mu$l.
Sodium chloride solution: 200 $\mu$l.
Reagent: 500 $\mu$l.

The first reading off $E_1$ is carried out 35 to 100 seconds after the start of the reaction and the second reading off 150 to 200 seconds later. With reference to a standard batch, the computer of the automatic device calculates the uric acid concentration ($c_{sample}$) according to the formula:

$$c_{sample} = \frac{c_{standard} \cdot (E_2 - E_1)_{sample}}{(E_2 - E_1)_{standard}} \text{ mMol/l.}$$

Sample material

Serum, plasma and diluted urine

The experiments were carried out analogously to Examples 1 to 27, with and without the use of the additives according to the present invention. The results obtained corresponded fully to those which were obtained with the corresponding additions according to Examples 1 to 27.

It will be understood that the specification and examples are illustrative but not limitative of the present invention and that other embodiments within the spirit and scope of the invention will suggest themselves to those skilled in the art.

What is claimed is:

1. In a process for the determination of uric acid by the uricase/catalase/aldehyde dehydrogenase method wherein the formation of reduced NAD(P)H is taken as a measure of the amount of uric acid present, the improvement comprising adding to the reagents, in an amount sufficient to suppress creep reactions in said method, at least one compound selected from the group consisting of trihaloethanols, pyrazole, pyridine, substituted pyrazole and pyridine wherein the substituents are selected from the group consisting of lower alkyl and halogen, pyridine carboxylic acids, pyridine carboxylic acids substituted with a lower alkyl radical, pyridine carboxylic acid amides and pyridine carboxylic acid lower alkyl esters, thiourea and isobutyramide.

2. Improvement as claimed in claim 1 wherein an oxalate is additionally added to the reagents.

3. Improvement as claimed in claim 1 wherein malonic acid mono-lower alkyl ester is additionally added to the reagents.

4. Improvement as claimed in claim 1 wherein said compound is a trihaloethanol.

5. Improvement as claimed in claim 1 wherein said compound is pyrazole or pyridine.

6. Improvement as claimed in claim 1 wherein said compound is pyrazole or pyridine substituted with at least one of lower alkyl and halogen.

7. Improvement as claimed in claim 1 wherein said compound is pyridine carboxylic acid or pyridine carboxylic acid substituted with lower alkyl.

8. Improvement as claimed in claim 1 wherein said compound is a pyridine carboxylic acid amide or pyridine carboxylic acid amide substituted with lower alkyl.

9. Improvement as claimed in claim 1 wherein said compound is a pyridine carboxylic acid lower alkyl ester, the pyridine moiety being optionally substituted with lower alkyl.

10. Improvement as claimed in claim 1 wherein said compound is thiourea.

11. Improvement as claimed in claim 1 wherein said compound is isobutyramide.

12. Improvement as claimed in claim 1 wherein said compound is used in an amount of from 0.005 to 0.5 Mol/liter of reagent.

13. Improvement as claimed in claim 1 wherein the reaction is carried out at a pH of from 8.0 to 9.0.

14. Reagent for the determination of uric acid, comprising uricase, catalase, aldehyde dehydrogenase, alcohol, NAD(P) and buffer, together with at least one additive compound selected from the group consisting of trihaloethanols, pyrazole and pyridine optionally substituted with one or more lower alkyl radicals and/or halogen atoms, pyridine-carboxylic acids optionally substituted by a lower alkyl radical and the amides and lower alkyl esters thereof, thiourea and isobutyramide in an amount sufficient to prevent creep reactions.

15. Reagent as claimed in claim 14 additionally containing an oxalate or a malonic acid mono-lower alkyl ester.

16. Reagent as claimed in claim 14 wherein said compound comprises about
$1 \times 10^2$ to $1 \times 10^3$ U/liter uricase,
500 to 1500 kU/liter catalase,
500 to 1000 U/liter aldehyde dehydrogenase,
0.3 to 2 Mol/liter ethanol,
0.5 to 1.5 mMol/liter $NAD^+$ or $NADP^+$,
20 to 100 mMol/liter buffer (pH 8.0 to 9.0) and
0.005 to 0.5 Mol/liter of additive.

17. In a process for the determination of uric acid by the uricase/catalase/aldehyde dehydrogenase method wherein the formation of reduced NAD(P)H is taken as a measure of the amount of uric acid present, the improvement comprising adding to the reagents, to suppress creep reactions, from 0.005 to 0.5 mol per liter of chelate forming complexing agents.

18. Improvement as claimed in claim 17 wherein said chelate-forming complexing agents are selected from the group consisting of nitrilotriacetic acid and ethylenediamine-tetraacetic acid.

19. Reagent for the determination of uric acid comprising uricase, catalase, aldehyde dehydrogenase, alcohol, NAD(P) and buffer together with from 0.005 to 0.5 mol per liter of chelate-forming complexing agents in an amount sufficient to prevent creep reactions.

* * * * *